United States Patent
Marti et al.

(10) Patent No.: US 9,298,994 B2
(45) Date of Patent: Mar. 29, 2016

(54) DETECTING VISUAL INATTENTION BASED ON EYE CONVERGENCE

(71) Applicant: HARMAN INTERNATIONAL INDUSTRIES, INC., Stamford, CT (US)

(72) Inventors: Stefan Marti, Oakland, CA (US); Davide Di Censo, San Mateo, CA (US)

(73) Assignee: Harman International Industries, Inc., Stamford, CT (US)

(*) Notice: Subject to any disclaimer, the term of this patent is extended or adjusted under 35 U.S.C. 154(b) by 122 days.

(21) Appl. No.: 14/151,670

(22) Filed: Jan. 9, 2014

(65) Prior Publication Data
US 2015/0193664 A1 Jul. 9, 2015

(51) Int. Cl.
| | |
|---|---|
| G06K 9/00 | (2006.01) |
| A61B 3/113 | (2006.01) |
| A61B 5/18 | (2006.01) |
| B60W 50/14 | (2012.01) |
| B60K 28/06 | (2006.01) |
| G08B 21/06 | (2006.01) |
| G01S 11/12 | (2006.01) |

(Continued)

(52) U.S. Cl.
CPC ............ *G06K 9/00845* (2013.01); *A61B 3/113* (2013.01); *A61B 5/18* (2013.01); *B60K 28/066* (2013.01); *B60W 50/14* (2013.01); *G01S 11/12* (2013.01); *G06K 9/00597* (2013.01); *G06K 9/00805* (2013.01); *G08B 21/06* (2013.01); *A61B 5/002* (2013.01); *A61B 5/1112* (2013.01); *A61B 5/746* (2013.01); *A61B 5/7455* (2013.01)

(58) Field of Classification Search
CPC .................................................. G06K 9/00845
USPC .......................................................... 382/103
See application file for complete search history.

(56) References Cited

U.S. PATENT DOCUMENTS

| | | | |
|---|---|---|---|
| 2010/0253526 A1 | 10/2010 | Szczerba et al. | |
| 2012/0215403 A1* | 8/2012 | Tengler et al. | 701/36 |

(Continued)

FOREIGN PATENT DOCUMENTS

| | | |
|---|---|---|
| EP | 1484014 A1 | 12/2004 |
| WO | 2004034905 A1 | 4/2004 |

OTHER PUBLICATIONS

"Introducing Tobii Technology," Tobii Technology, accessed Mar. 31, 2013, www.tobii.com.
"Simultaneous localization and mapping," Wikipedia.com, page last modified Feb. 25, 2014, 6 pages, http://en.wikipedia.org/wiki/Simultaneous_localization_and_mapping.

(Continued)

*Primary Examiner* — Stephen R Koziol
*Assistant Examiner* — Delomia L Gilliard
(74) *Attorney, Agent, or Firm* — Artegis Law Group, LLP (57) ABSTRACT

One embodiment of the present invention sets forth a technique for detecting when a user is not being attentive based on eye convergence. The technique includes determining a first distance from the user to a first object. The first distance may be determined using a depth sensor. The technique further includes determining a first vergence angle associated with a left eye of the user and determining a second vergence angle associated with a right eye of the user. The technique further includes determining a first eye convergence distance based on the first vergence angle, the second vergence angle, and an interocular distance between the left eye and the right eye. The technique further includes comparing the first distance to the first eye convergence distance to generate a first result. An inattention alert may be generated based on the first result.

20 Claims, 7 Drawing Sheets

(51) Int. Cl.
  *A61B 5/00*  (2006.01)
  *A61B 5/11*  (2006.01)

(56) References Cited

U.S. PATENT DOCUMENTS

2014/0022246 A1*  1/2014  Ono et al. .................... 345/419
2015/0109429 A1*  4/2015  Inoue et al. .................... 348/78

OTHER PUBLICATIONS

Extended European Search Report for Application No. 15150488.3 dated May 21, 2015.

Green et al., "Modelling on-line adaptation of the VOR gain with target distance and eccentricity", Engineering in Medicine and Biology Society, 1995, IEEE 17th Annual Conference Montreal, Quebec, Canada, Sep. 20-23, 1995, New York, New York, vol. 2, pp. 1459-1460.

* cited by examiner

DETECTING VISUAL INATTENTION BASED ON EYE CONVERGENCE

BACKGROUND

1. Field of the Embodiments of the Invention

Embodiments of the present invention generally relate to eye gaze tracking and, more specifically, to detecting visual inattention based on eye convergence.

2. Description of the Related Art

Approximately ten million people are involved in automobile accidents each year in the United States. Although a variety of factors may contribute to the occurrence of an automobile accident, driver inattention is the leading cause. In some cases, driver inattention may result from distractions inside of an automobile, such as operation of a cell phone, distractions outside of the automobile, or driver fatigue.

In order to reduce the incidence of automobile accidents resulting from driver inattention, car manufacturers have begun to introduce technologies that perform head tracking. For example, various safety systems track the location of the driver's head and determine whether the position of the head has deviated from a particular location, indicating that the driver is falling asleep. In response, the safety system may provide a visual and/or auditory warning to the driver. Additionally, various safety systems detect the direction of the driver's head and provide a visual and/or auditory warning if the driver is looking away from the road.

However, the safety systems described above are unable to detect situations in which a driver is looking towards the road ahead but is not paying attention to what is in front of him or her. That is, the direction of a driver's head is not necessarily indicative of the attentiveness of the driver. As a result, such systems may be unable to detect when a driver is daydreaming and/or otherwise failing to pay attention to his or her surroundings.

As the foregoing illustrates, improved techniques for enabling the detection of driver inattentiveness would be useful.

SUMMARY

One embodiment of the present invention sets forth a method for detecting when a user is not being attentive based on eye convergence. The method includes determining a first distance from the user to a first object. The method further includes determining a first vergence angle associated with a left eye of the user and determining a second vergence angle associated with a right eye of the user. The method further includes determining a first eye convergence distance based on the first vergence angle, the second vergence angle, and an interocular distance between the left eye and the right eye. The method further includes comparing the first distance to the first eye convergence distance to generate a first result.

Further embodiments provide, among other things, a tracking system and a non-transitory computer-readable medium configured to carry out method steps set forth above.

Advantageously, the disclosed techniques enable the detection of types of user inattentiveness that cannot be detected using conventional techniques. Additionally, the disclosed techniques are context sensitive, tracking both the direction in which the user is looking and the object(s) are which the user is looking. Accordingly, by tracking and responding to user inattentiveness, user safety is increased.

BRIEF DESCRIPTION OF THE SEVERAL VIEWS OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the embodiments of the present invention. However, it will be apparent to one of skill in the art that the embodiments of the present invention may be practiced without one or more of these specific details.

Figure 1A:
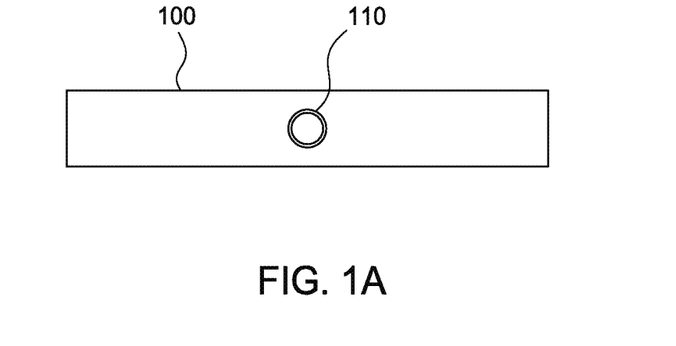
FIGS. 1A and 1B are conceptual diagrams of an eye tracking device, according to various embodiments of the present invention.
Figure 1B:
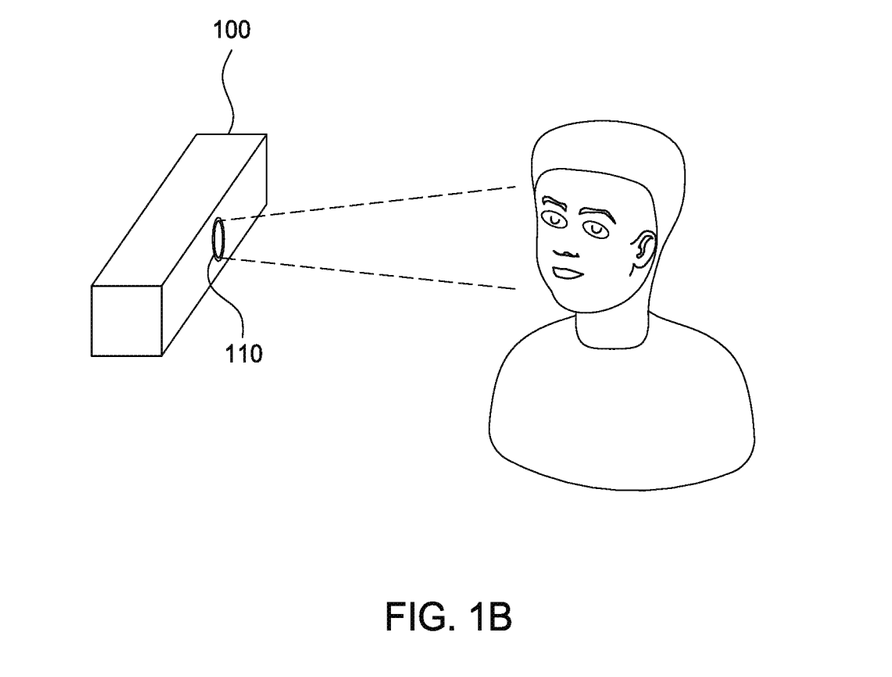

FIGS. 1A and 1B are conceptual diagrams of an eye tracking device 100, according to various embodiments of the present invention. As shown, the eye tracking device 100 may include, without limitation, one or more cameras 110 configured to acquire images and/or determine the position of a user. Images acquired by the one or more cameras 110 may be analyzed by a computing device 120 included in the eye tracking device 100 and/or a computing device 120 that is separate from the eye tracking device 100.

In various embodiments, images acquired by the camera 110 may be used to determine the eye position(s) of a user's left eye and/or right eye. For example, as shown in FIG. 1B, the camera 110 may be configured to acquire images of a user's eyes or face. The images may then be analyzed to determine eye position(s), eye vergence angle(s), two-dimensional (2D) vectors, three-dimensional (3D) vectors, and/or the focal point and/or distance at which the eyes converge. In some embodiments, images of the user's eyes are processed using pupil center corneal reflection eye tracking techniques, such as those implemented in the "Eye Trackers" produced by TOBII TECHNOLOGY™ (Fall Church, Va., USA). Additionally, in various embodiments, the eye tracking device 100 may include multiple cameras 110. In some embodiments, the eye tracking device 100 includes at least two cameras 110, each of which is configured to track one or both of the user's eyes. Further, additional cameras 110 and/or sensors (e.g., light sensors, image sensors, depth sensors, etc.) may be included in the eye tracking device 100 to measure the distance from the user to the eye tracking device 100, the distance of various objects from the eye tracking device 100, and the like.

In some embodiments, the eye tracking device 100 is worn by the user. For example, and without limitation, the eye tracking device 100 may be a headset or pair of glasses worn by the user. In such embodiments, a camera 110 could be positioned in the eye tracking device 100 proximate to the user's eyes. For example, one or more cameras 110 may be positioned in a headset or pair of glasses near each of the user's eyes.

Figure 2A:
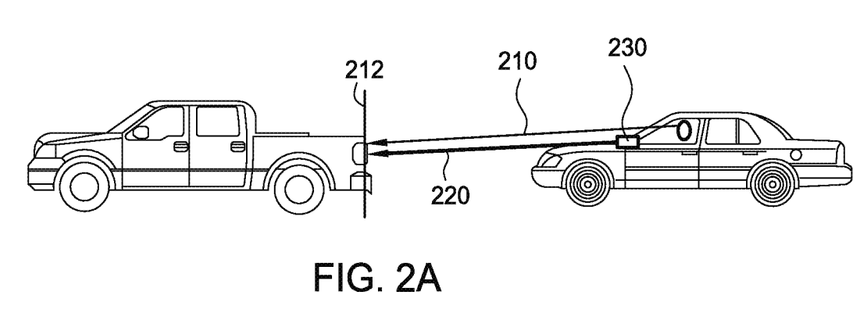
FIGS. 2A and 2B are conceptual diagrams illustrating eye focal points of a driver of a vehicle, according to various embodiments of the present invention.
Figure 2B:
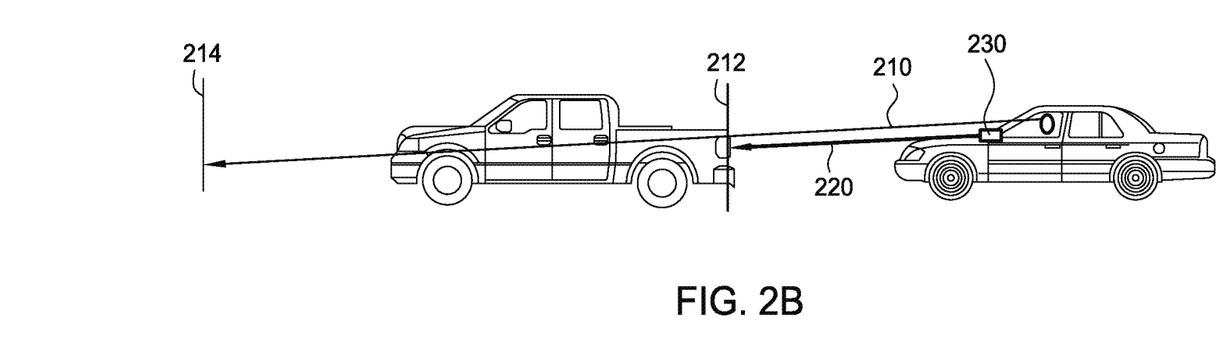

FIGS. 2A and 2B illustrate eye focal points 212, 214 of a driver of a vehicle, according to various embodiments of the present invention. As described above, conventional safety systems are unable to detect situations in which a driver is looking towards an object but is not paying attention to the object. For example, with respect to FIG. 2A, the driver's head is facing forward, and the driver's eyesight 210 is focused on a location 212 of a vehicle in front of the driver. However, as shown in FIG. 2B, if the driver stops paying attention to the vehicle, such as when the driver is daydreaming, the driver's head may continue to face forward, but he or she may not be focusing on, or paying attention to, the vehicle. In some cases, the driver may look through the vehicle without focusing on the vehicle. Under such circumstances, the eye tracking device 100 may be used to determine the location and/or distance at which the driver's eyes converge.

In various embodiments, a depth sensor 230 may be used to determine a distance to an object that is located in the field of view of the driver. The eye tracking device 100 may then acquire one or more images of the driver's eyes and analyze the images to determine the distance and/or location at which the driver's eyes converge. The object distance determined by the depth sensor 230 may then be compared to the eye convergence distance to determine that, instead of focusing on the object at location 212, the driver is focusing on location 214. In response, the eye tracking device 100 may determine that the driver is not paying attention to the vehicle and/or other relevant objects in the surrounding area and may provide an auditory, visual, and/or other type of alert (e.g., a vibration alert) to the driver to allow the driver to refocus his or her attention.

The depth sensor 230 may determine the distance to one or more objects in the surrounding area using a variety of techniques. These techniques may include, without limitation, optical techniques, time-of-flight techniques, global positioning system (GPS) techniques, stereoscopic techniques, and the like. Additionally, the depth sensor 230 may be positioned in a variety of locations relative to the location of the driver's eyes. For example, although FIGS. 2A and 2B depict the depth sensor 230 as being located in front of the driver, near the hood of the vehicle, in other embodiments, the depth sensor 230 may be located at another position on the exterior of the vehicle or in the interior of the vehicle. Moreover, when the depth sensor 230 is located in the interior of the vehicle, the depth sensor 230 may be located in front of the driver, behind the driver, or next to the driver. In various embodiments, the depth sensor 230 is positioned at a location that is near, or in line with, the driver's eyes and/or the driver's eyesight 210 (e.g., on a headset or pair of glasses). By positioning the depth sensor 230 near, or in line with, the driver's eyes and/or the driver's eyesight 210, the depth sensor 230 line-of-sight 220 may more accurately reflect the driver's viewpoint, enabling the depth sensor to more accurately determine the object at which the driver's eye gaze is directed. Alternatively, if the depth sensor 230 is not near the driver's eyes and/or not in line with the driver's eyesight 210, then the distance(s) determined by the depth sensor 230 may be processed to compensate for such differences. For example, and without limitation, if the depth sensor 230 is positioned at a location that is in front (or behind) of the driver, then the distance(s) determined by the depth sensor 230 may be processed to compensate for the distance between the driver and the depth sensor 230. After processing, the object distance(s) may then be compared to the eye convergence distance(s) acquired by the eye tracking device 100. In other embodiments, if the depth sensor 230 is positioned next to the driver, then the distance(s) determined by the depth sensor 230 may be processed to compensate for the difference in viewpoint (e.g., an angular difference) between the driver and the depth sensor 230.

In various embodiments, the depth sensor 230 may determine the distance to an object in the surrounding environment by accessing a database (e.g., a geographical information database) and/or a vehicle-to-vehicle protocol. In some embodiments, the depth sensor 230 may include a communication device and/or database that is configured to receive and store information associated with the locations of objects in the surrounding environment. For example, and without limitation, the depth sensor 230 may receive location information (e.g., GPS data) of an object in the surrounding environment and use the location information to determine the distance between the driver and the object. Such communications may be transmitted through a mobile network, such as a cellular network, or through a wireless protocol, such as a vehicle-to-vehicle or peer-to-peer protocol. Accordingly, the depth sensor 230 may rely on techniques other than optical techniques, time-of-flight techniques, etc. to determine the distance between the driver and an object in the surrounding environment. In such embodiments, the depth sensor 230 may be located in any practical position relative to the driver.

Figure 3:
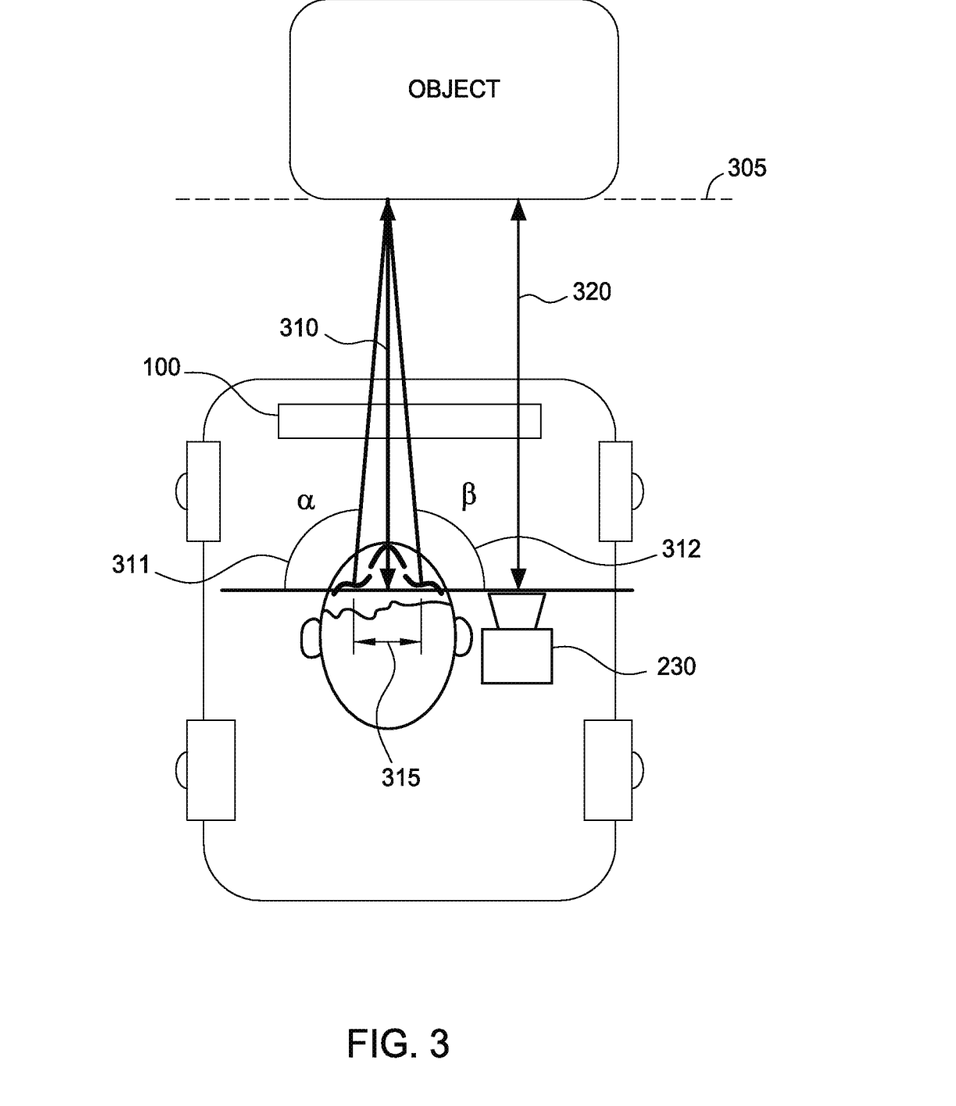
FIG. 3 is a conceptual diagram illustrating a technique for determining an object distance and an eye convergence distance, according to various embodiments of the present invention.

FIG. 3 is a conceptual diagram illustrating a technique for determining an object distance and an eye convergence distance, according to various embodiments of the present invention. In general, when a driver is operating a vehicle, the most relevant objects are located in front of the driver. For example, a driver must pay attention to objects in front of him or her in order to brake at appropriate times, in order to keep his or her vehicle within a traffic lane, and in order to avoid hitting objects, such as other vehicles and pedestrians. Consequently, in some embodiments, the depth sensor 230 may be configured to determine the distance 320 to objects that are in located front of the driver.

In operation, the depth sensor 320 determines one or more distances 320 between the driver and one or more objects in front of the driver. The eye tracking device 100 then determines the distance 310 to the location 305 at which the driver's eyes converge. The eye convergence distance 310 is then compared to the object distance(s) 320 to determine whether the driver is paying attention to an object that is located in the driver's eye gaze. In various embodiments, a computing device 120 included in the eye tracking device 100 (or included in a device that is separate from the eye tracking device 100) determines whether driver is paying attention to an object located in the driver's eye gaze by determining whether the eye convergence distance 310 is substantially similar to the one or more object distances 320. As described above, prior to comparing an object distance 320 to the eye convergence distance 310, one or both of the distances 310, 320 may be processed to account for a difference in viewpoint between the driver and the depth sensor 230. If the eye convergence distance 310 is not substantially similar to an object distance 320, then the computing device 120 may determine that the driver is not paying attention to the object(s). Based on this result, an auditory, visual, tactile, and/or electromechanical alert may then be issued to the driver to provide the driver with an opportunity to focus his or her attention on the surrounding area.

In other embodiments, more advanced techniques for comparing the eye convergence distance 310 to the object distances 320 may be used in order to determine whether an alert should be issued to the driver. For example, the computing device 120 may determine that an alert should be issued to the driver if the eye convergence distance 310 is not substantially similar to an object distance 320 a threshold number of times and/or for a threshold duration of time. Such implementations may account for occasional inaccuracies associated with the eye tracking device 100 or depth sensor 230 and/or allow the driver to refocus his or her attention on the surrounding area after brief periods of inattention without receiving an alert.

In various embodiments, eye convergence distance 310 may be determined based on the interocular distance 315 between the driver's eyes and the vergence angles 311, 312 of one or both of the driver's eyes. For example, the eye tracking techniques described above, such as, without limitation, a pupil center corneal reflection eye tracking technique, may be used to determine the vergence angles 311, 312 and/or the interocular distance 315 of the driver's eyes. The vergence angles 311, 312 and the interocular distance 315 may then be inputted into one or more trigonometric formulas, algorithms, lookup tables, etc. to determine the distance 310 to the location at which the driver's eye converge, as described in further detail in conjunction with FIG. 5.

Figure 4:
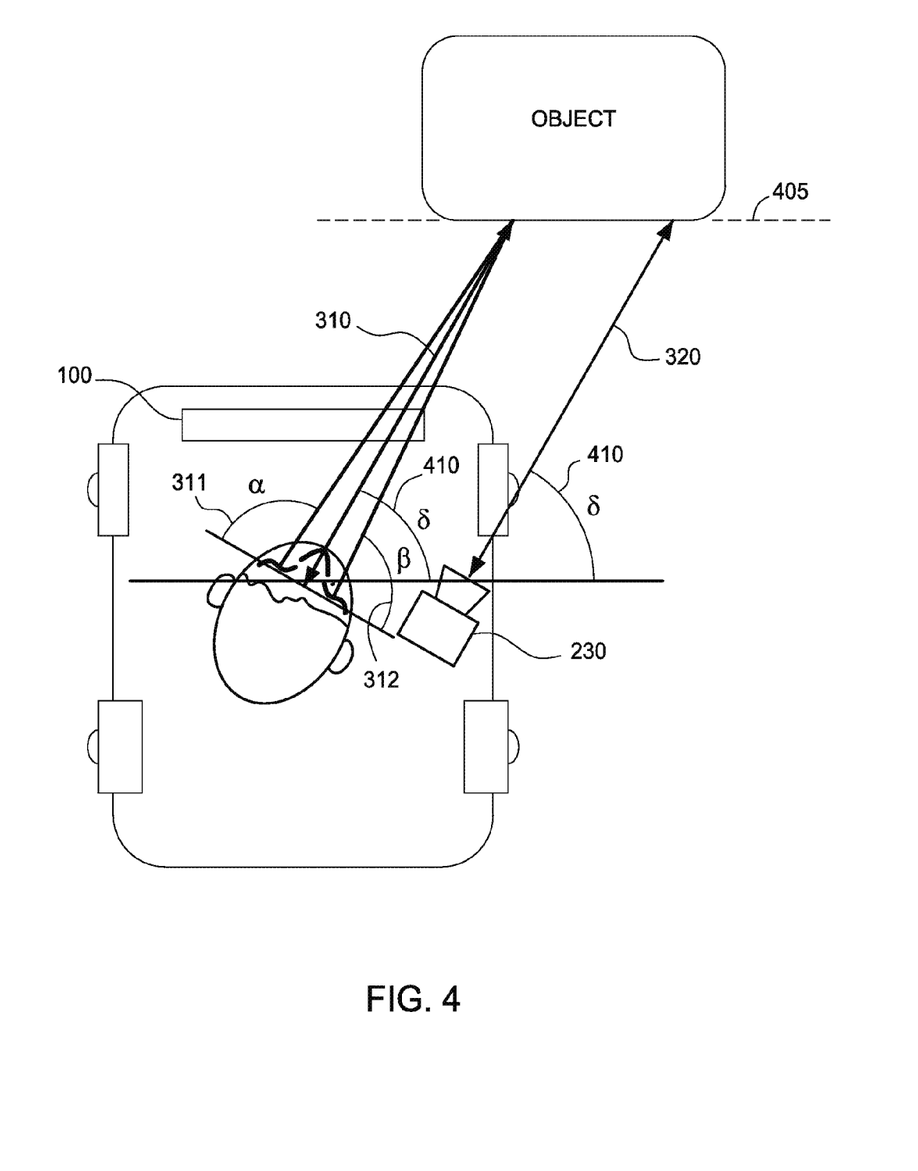
FIG. 4 is a conceptual diagram illustrating a technique for positioning a depth sensor to determine an object distance, according to various embodiments of the present invention.

FIG. 4 is a conceptual diagram illustrating a technique for positioning a depth sensor to determine an object distance, according to various embodiments of the present invention. As shown, in various embodiments, the depth sensor 230 may be positioned based on the eye gaze direction of the driver in order to more accurately determine the distance 320 to objects located in the eye gaze direction. Accordingly, a more accurate comparison may be made between the driver's eye convergence distance 310 and an object distance 320 when the object is not located directly in front of the driver.

In various embodiments, the depth sensor 230 may be positioned based on images and/or measurements acquired by the eye tracking device 100. For example, and without limitation, the eye tracking device 100 may acquire one or more images to determine an eye gaze direction and/or vergence angle(s) 311, 312 of the driver. The depth sensor 230 may then be configured to rotate, pivot, slide, etc. to an appropriate position based on the eye gaze direction and/or vergence angle(s) 311, 312 in order to more accurately determine the distance 320 to an object based on the driver's perspective. In other embodiments, the eye gaze direction of the driver may be determined using one or more sensors included in the depth sensor 230 or in a separate device.

In some embodiments, the depth sensor 230 is configured to rotate to match the orientation of the driver's eye gaze direction. For example, as shown in FIG. 4, the angle 410 of the depth sensor 230 relative to an arbitrary plane may be substantially similar to the angle 410 of the driver's eye gaze direction relative to the arbitrary plane. In other embodiments, the direction of the depth sensor 230 may be substantially similar to the direction that the driver's head is facing. Since a driver typically moves his or her head less frequently than his or her eyes, tracking and responding to changes in the driver's head direction, instead of eye gaze direction, may reduce power consumption and/or electromechanical requirements by reducing the frequency and/or speed with which the depth sensor 230 is repositioned. In still other embodiments, the depth sensor 230 may be located on the driver, such as on the driver's face, chest, shoulders, etc. For example, the depth sensor 230 may be located on a headset or pair of glasses worn by the driver. In such embodiments, the depth sensor 230 may determine object distances 320 using any of the techniques described above, including optical techniques, time-of-flight techniques, GPS techniques, database techniques, stereoscopic techniques, and the like.

Figure 5:
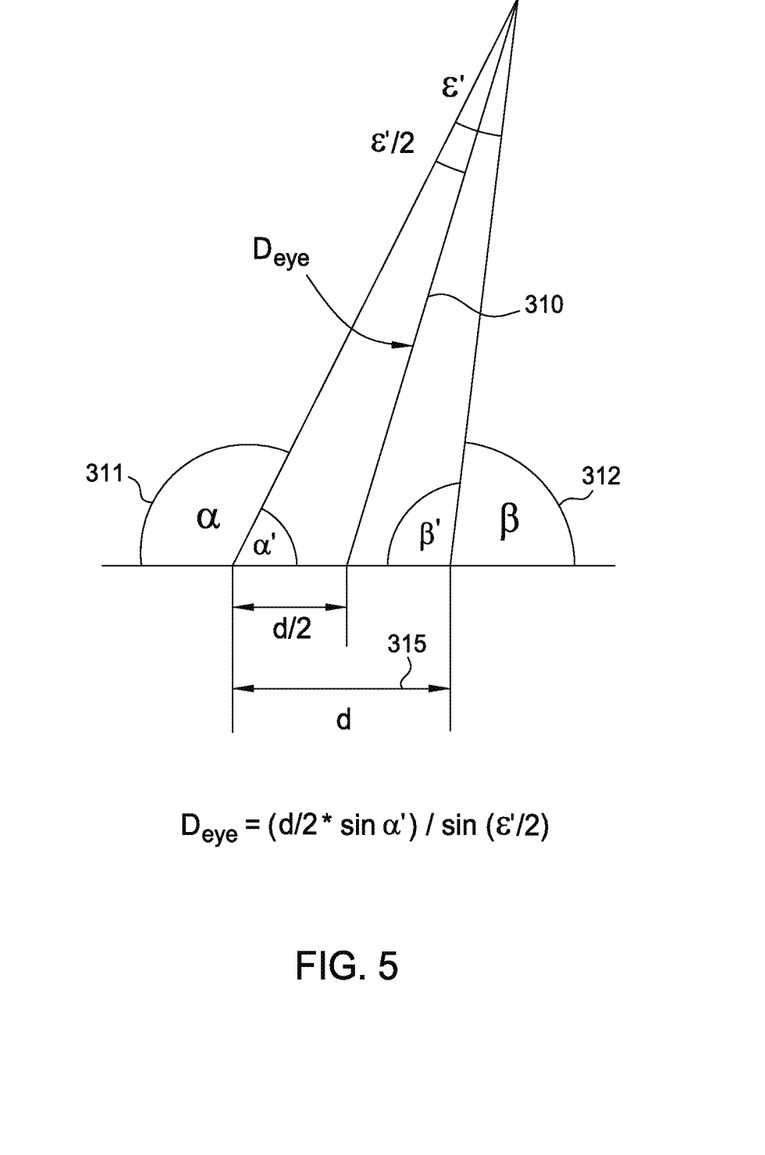
FIG. 5 is a conceptual diagram illustrating a technique for determining an eye convergence distance, according to various embodiments of the present invention.

FIG. 5 is a conceptual diagram illustrating a technique for determining an eye convergence distance 310, according to various embodiments of the present invention. As shown, and as described in conjunction with FIGS. 3 and 4, a vergence angle 311, 312 may be determined for the driver's eyes. The vergence angles 311, 312 and the interocular distance 315 may then be used to determine the eye convergence distance using Equation 1, reproduced below. In other embodiments, other equations or algorithms, lookups tables, and the like may be used to determine eye convergence distance 310.

$$D_{eye} = (d/2 * \sin \alpha')/\sin(\epsilon'/2) \quad \text{(Eq. 1)}$$

Figure 6:
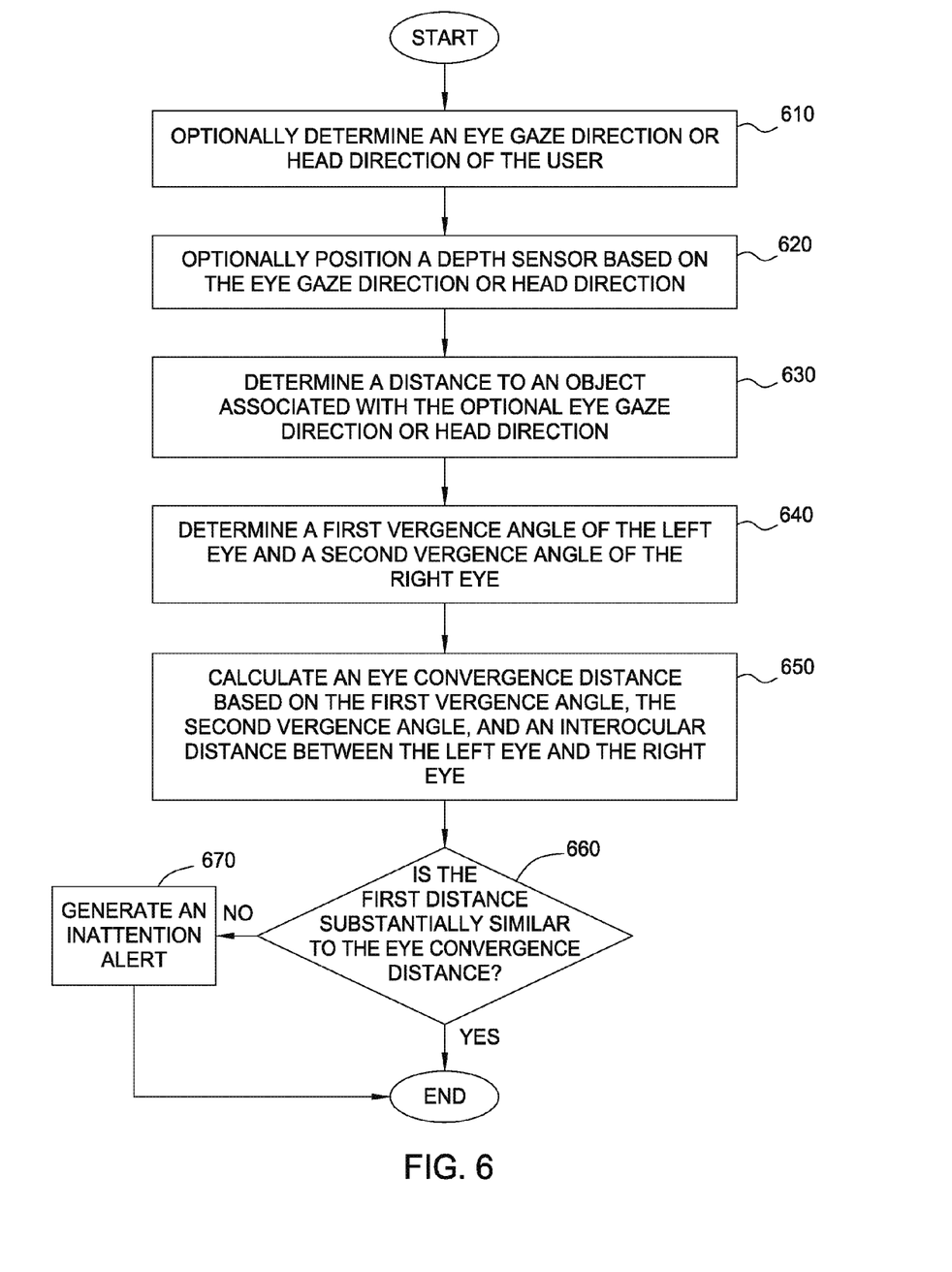
FIG. 6 is a flow diagram of method steps for detecting visual inattention based on eye convergence, according to various embodiments of the present invention.

FIG. 6 is a flow diagram of method steps for detecting visual inattention based on eye convergence, according to various embodiments of the present invention. Although the method steps are described in conjunction with FIGS. 1-5, persons skilled in the art will understand that any system configured to perform the method steps, in any order, falls within the scope of the present invention.

As shown, a method 600 begins at step 610, where the eye tracking device 100 (or a separate device) optionally determines an eye gaze direction and/or head direction of the user. At step 620, the depth sensor 230 is optionally positioned based on the eye gaze direction and/or head direction of the user. As described above, in other embodiments, the depth sensor 230 may be fixed to a vehicle, to the user (e.g., on a headset, glasses, or other similar wearable apparatus), or to another object. In such embodiments, the depth sensor 230 may not be electromechanically repositioned.

Next, at step 630, the depth sensor 230 determines a distance 320 to an object associated with the eye gaze direction and/or head direction of the user. At step 640, vergence angles 311, 312 are determined for the user's eyes. Optionally, an interocular distance 315 may be determined at step 640. Then, at step 650, the computing device 120 determines an eye convergence distance 310 based on the vergence angle(s) 311, 312 and the interocular distance 315.

At step 660, the computing device 120 compares the eye convergence distance 310 to the object distance 320 to determine whether the distances 310, 320 are not substantially similar. If the distances 310, 320 are not substantially similar, then the method 600 proceeds to step 670, where the eye tracking device 100, depth sensor 230, and/or a separate device generates an alert. In various embodiments, the alert may include an auditory and/or visual alert, such as an alert light, an alert message, and/or an alert sound. Additionally, other types of alerts, such as vibrations and alerts that utilize other types of physical actuators and/or vibration motors, may be used to get the user's attention. If, at step 660, the computing device 120 determines that the distances 310, 320 are substantially similar, then the method 600 ends.

Figure 7:
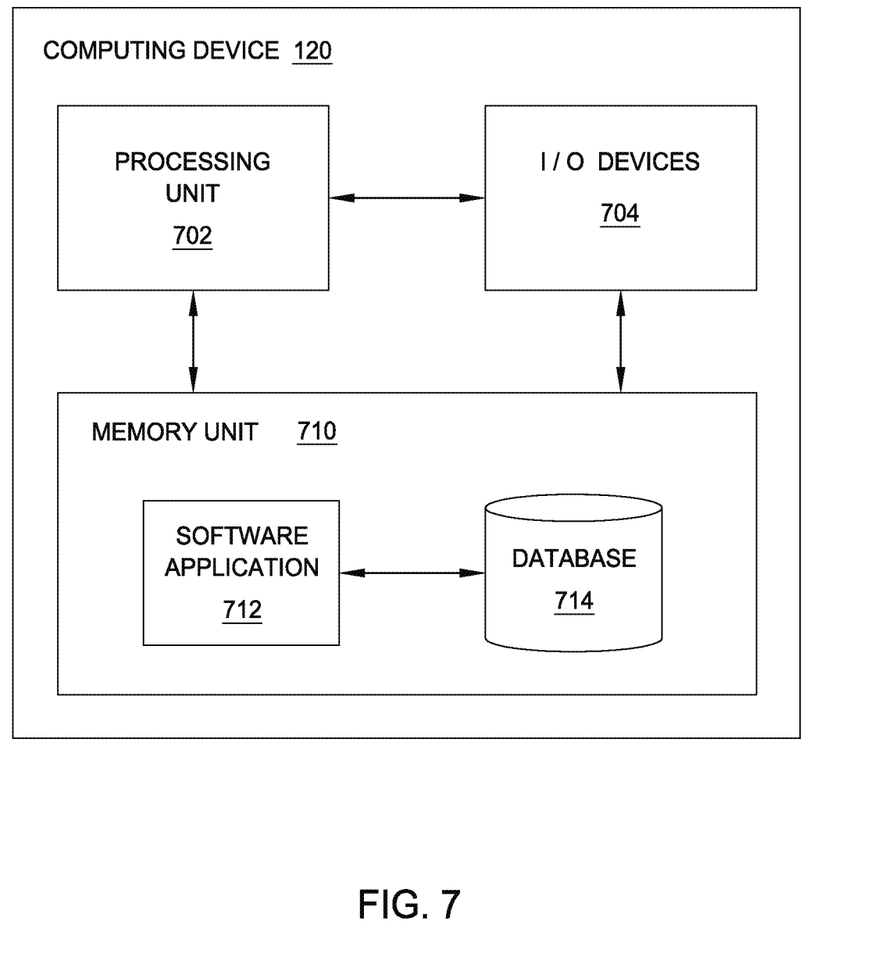
FIG. 7 is a block diagram illustrating a computer system configured to implement one or more aspects of the present invention.

FIG. 7 is a block diagram illustrating a computer system configured to implement one or more aspects of the present invention. As shown, computing device 120 includes a processing unit 702, input/output (I/O) devices 704, and a memory unit 710. Memory unit 710 includes an application 712 configured to interact with a database 714.

Processing unit 702 may include a central processing unit (CPU), digital signal processing unit (DSP), and so forth. I/O devices 704 may include input devices, output devices, and devices capable of both receiving input and providing output. Memory unit 710 may include a memory module or a collection of memory modules. Software application 712 within memory unit 710 may be executed by processing unit 702 to implement the overall functionality of computing device 120, and, thus, to coordinate the operation of the eye tracking device 100 and/or depth sensor 230 as a whole. The database 714 may store interocular distances, GPS coordinates, object locations, object distances, lookup tables, and other data for computing and comparing object distances 320 and eye convergence distances 310.

Computing device 120 may be coupled to a sensor array that includes one or more sensors, such as one or more cameras 110 and/or depth sensors 230. The sensor array is configured to measure various properties of the environment within which user resides, as well as various properties associated with user (e.g., orientation, eye vergence angles, eye gaze direction). The sensor array may include any number of cameras 110, depth sensors, light sensors, electrical field detectors, compasses, gyroscopes, radio transceivers, global positioning system (GPS) receivers, or any other type of sensor. Generally, the sensor array captures sensory data associated with the environment and sensory data associated with user, and provides that data to computing device 120.

Computing device 120 may also be coupled to audio output devices associated with the eye tracking device 100 and/or depth sensor 230 that include one or more devices, such as speakers, configured to generate acoustic output (e.g., an auditory alert) to the user. The audio output devices may include any number of speakers, headphones, audio devices, or any other type of device capable of generating sound.

Computing device 120 as a whole may be a microprocessor, an application-specific integrated circuit (ASIC), a system-on-a-chip (SoC), a mobile computing device such as a tablet computer or cell phone, a media player, and so forth. Generally, computing device 120 is configured to coordinate the overall operation of the eye tracking device 100 and/or depth sensor 230. Any technically feasible system configured to implement the functionality of the eye tracking device 100 and/or depth sensor 230 falls within the scope of the present invention.

In sum, the depth sensor determines the distance from the user to an object proximate to the user's eye gaze. The eye tracking device then determines the vergence angles of the user's eyes, and an eye convergence distance is determined based on the vergence angles and the user's interocular distance. Next, the computing device determines whether the eye convergence distance is substantially similar to the distance from the user to the object. If the eye convergence distance is not substantially similar to the object distance, then the computing device determines that the user is not paying attention to his or her surroundings. In response, an alert is generated.

One advantage of the techniques described herein is that types of user inattentiveness can be detected that could not be detected using conventional techniques. Additionally, the disclosed techniques are context sensitive, tracking both the direction in which the user is looking and the object(s) are which the user is looking. Accordingly, by tracking and responding to user inattentiveness, user safety is increased.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as compact disc read only memory (CD-ROM) disks readable by a CD-ROM drive, flash memory, read only memory (ROM) chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments. Persons of ordinary skill in the art, however, will understand that various modifications and changes may be made thereto without departing from the broader spirit and scope of the invention as set forth in the appended claims. For example, although many of the descriptions herein refer to the user as a driver of a vehicle, persons skilled in the art will appreciate that the systems and techniques described herein are applicable to other situations (e.g., non-vehicular) in which the determination of the eye gaze characteristics of a user and object distances may enhance user safety and/or user experience. The foregoing description and drawings are, accordingly, to be regarded in an illustrative rather than a restrictive sense.

Therefore, the scope of embodiments of the present invention is set forth in the claims that follow.

What is claimed is:

1. A computer-implemented method for detecting when a user is not being attentive based on eye convergence, the method comprising:
   determining, via a depth sensor, a first distance between a location associated with a vehicle and a first object located outside of the vehicle;
   determining a second distance from the user to the first object based on the first distance;
   determining a first vergence angle associated with a left eye of the user;
   determining a second vergence angle associated with a right eye of the user;
   determining a first eye convergence distance based on the first vergence angle, the second vergence angle, and an interocular distance between the left eye and the right eye; and
   comparing the second distance to the first eye convergence distance to generate a first result.

2. The method of claim 1, wherein comparing the second distance to the first eye convergence distance comprises determining whether the second distance is substantially similar to the first eye convergence distance.

3. The method of claim 2, wherein the second distance is not substantially similar to the first eye convergence distance, and further comprising generating an inattention alert for the user based on the first result.

4. The method of claim 1, wherein determining the first distance comprises acquiring a depth measurement to the first object, and the depth sensor comprises at least one of a time-of-flight depth sensor and an optical depth sensor.

5. The method of claim 1, wherein determining the first distance comprises accessing at least one of global positioning system (GPS) data, a vehicle-to-vehicle communication protocol, a peer-to-peer communication protocol, and a geographical information database to read a distance value.

6. The method of claim 1, further comprising:
   determining an eye gaze direction of the user;
   determining a third distance from the user to a second object associated with the eye gaze direction;

determining a third vergence angle associated with the left eye of the user based on the eye gaze direction;
determining a fourth vergence angle associated with the right eye of the user based on the eye gaze direction;
determining a second eye convergence distance based on the third vergence angle, the fourth vergence angle, and the interocular distance; and
comparing the third distance to the second eye convergence distance to generate a second result.

7. The method of claim 6, further comprising, prior to determining the third distance, positioning the depth sensor based on at least one of the eye gaze direction and a user head direction, and wherein determining the first distance to the first object comprises acquiring a depth measurement to the first object with the depth sensor.

8. The method of claim 1, wherein determining the first vergence angle comprises tracking a left pupil of the user, and determining the second vergence angle comprises tracking a right pupil of the user.

9. The method of claim 1, wherein determining the first vergence angle comprises determining a first three-dimensional vector associated with a left pupil of the user, and determining the second vergence angle comprises determining a second three-dimensional vector associated with a right pupil of the user.

10. A system for tracking user attentiveness, comprising:
a depth sensor configured to determine a first distance between a location associated with a vehicle and a first object located outside of the vehicle;
an image sensor configured to acquire one or more images of a user; and
a processor configured to:
determine a second distance from the user to the first object based on the first distance;
determine a first vergence angle associated with a left eye of the user based on the one or more images;
determine a second vergence angle associated with a right eye of the user based on the one or more images;
determine a first eye convergence distance based on the first vergence angle, the second vergence angle, and an interocular distance between the left eye and the right eye; and
determine whether the second distance is substantially similar to the first eye convergence distance to generate a first result.

11. The system of claim 10, wherein the second distance is not substantially similar to the first eye convergence distance, and the processor is further configured to cause an inattention alert to be generated for the user based on the first result.

12. The system of claim 11, further comprising an alert device configured to generate the inattention alert, wherein the alert device comprises at least one of a speaker, a light-emitting device, and a vibration motor.

13. The system of claim 10, wherein the depth sensor is configured to determine the first distance by performing at least one of a time-of-flight depth measurement and an optical depth measurement.

14. The system of claim 10, wherein the depth sensor is configured to determine the first distance by accessing at least one of global positioning system (GPS) data, a vehicle-to-vehicle communication protocol, a peer-to-peer communication protocol, and a geographical information database to read a distance value.

15. The system of claim 10, wherein:
the depth sensor is further configured to determine a third distance between the location associated with the vehicle and a second object associated with an eye gaze direction of the user and located outside of the vehicle; and
the processor is further configured to:
determine the eye gaze direction of the user based on the one or more images;
determine a fourth distance from the user to the second object based on the third distance;
determine a third vergence angle associated with the left eye of the user based on the one or more images;
determine a fourth vergence angle associated with the right eye of the user based on the one or more images;
determine a second eye convergence distance based on the third vergence angle, the fourth vergence angle, and the interocular distance; and
compare the fourth distance to the second eye convergence distance to generate a second result.

16. The system of claim 15, wherein the depth sensor is further configured to, prior to determining the third distance, reposition based on at least one of the eye gaze direction and a user head direction.

17. The system of claim 16, wherein the depth sensor is configured to determine the third distance by performing at least one of a time-of-flight depth measurement and an optical depth measurement.

18. The system of claim 10, wherein the processor is configured to determine the first vergence angle by analyzing a left pupil of the user based on the one or more images, and determine the second vergence angle by analyzing a right pupil of the user based on the one or more images.

19. The system of claim 18, wherein the processor is further configured to determine the first vergence angle by determining a first three-dimensional vector associated with a left pupil of the user, and determine the second vergence angle by determining a second three-dimensional vector associated with a right pupil of the user.

20. A non-transitory computer-readable storage medium including instructions that, when executed by a processor, cause the processor to detect when a user is not being attentive based on eye convergence, by performing the steps of:
determining, via a depth sensor, a first distance between a location associated with a vehicle and a first object located outside of the vehicle;
determining a second distance from the user to the first object based on the first distance;
determining a first vector associated with a left eye of the user;
determining a second vector associated with a right eye of the user;
determining a first eye convergence distance based on the first vector, the second vector, and an interocular distance between the left eye and the right eye;
comparing the second distance to the first eye convergence distance to generate a first result; and
causing an inattention alert to be generated based on the first result.

* * * * *